United States Patent [19]

Moisson

[11] Patent Number: 4,959,196
[45] Date of Patent: Sep. 25, 1990

[54] DEVICE FOR BLOOD SAMPLING AND ANALYSIS

[75] Inventor: Claude Moisson, Nogent le Phaye, France

[73] Assignee: Biovallees, Monastier Sur Gazelle, France

[21] Appl. No.: 286,798

[22] Filed: Dec. 20, 1988

[30] Foreign Application Priority Data

Dec. 21, 1987 [FR] France .................. 87 17811

[51] Int. Cl.$^5$ .................. G01N 21/75; G01N 33/72; A61B 5/14; A61B 5/20
[52] U.S. Cl. .................. 422/82.05; 128/632; 128/770; 422/55; 422/58; 436/66; 436/67; 604/130; 604/137
[58] Field of Search .................. 422/68, 44, 55, 56, 422/58, 119; 436/44, 45, 46, 66, 67; 128/329 R, 632, 770, 314; 604/130, 137, 187, 318, 404

[56] References Cited

U.S. PATENT DOCUMENTS 4,469,110 9/1984 Slama .................. 128/770
4,637,403 1/1987 Garcia et al. .................. 128/770

Primary Examiner—Robert J. Warden
Assistant Examiner—Kimberly A. Trautman
Attorney, Agent, or Firm—Mason, Fenwick & Lawrence

[57] ABSTRACT

The invention relates to a device for sampling and analyzing blood. It comprises an auto-pricker (1), a magazine (2) for strips, these strips comprising a reactive zone, and a reflectometer (6). Moreover, the magazine (2) is integral with the auto-pricker (1) and the device comprises means (7, 8) enabling the reflectometer (6) and the auto-pricker (1) to be made integral at rest.

11 Claims, 4 Drawing Sheets

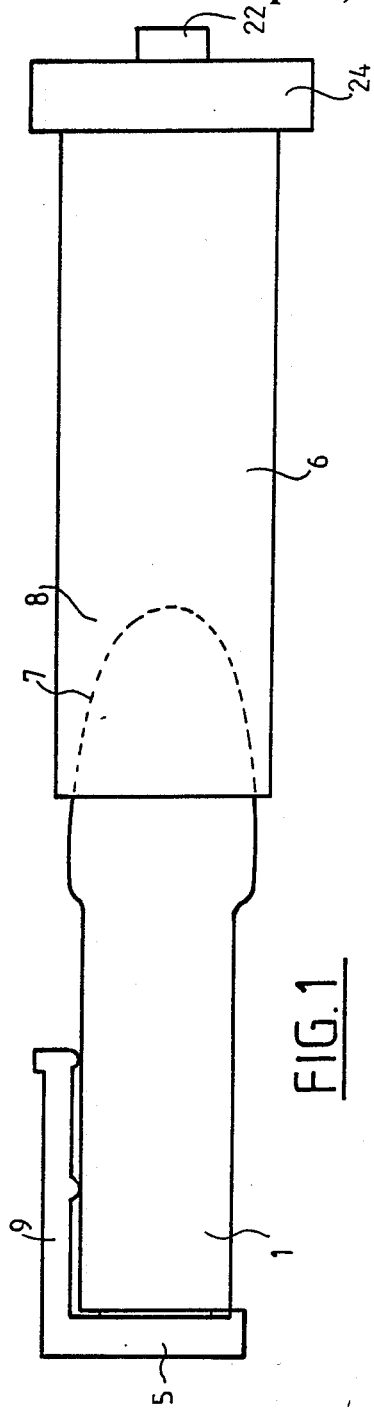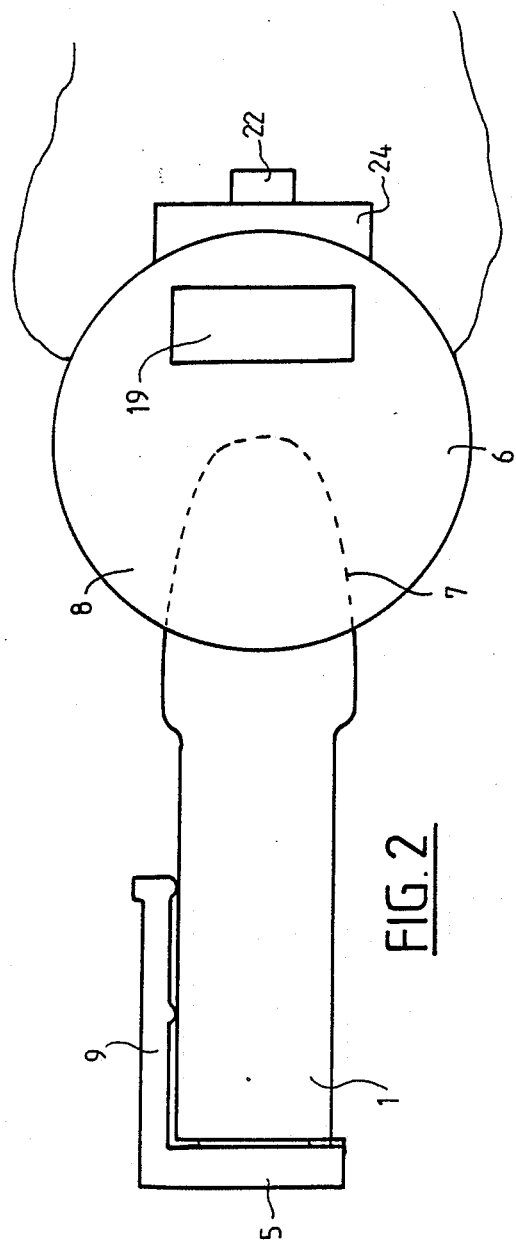

DEVICE FOR BLOOD SAMPLING AND ANALYSIS

FIELD OF THE INVENTION

Blood analyses are performed with increasing frequency both in a hospital environment and by doctors, by nurses or specialized laboratories or else the patient himself.

PRIOR ART

Blood concentrations of various components such as sugar, cholesterol and in general, all hormones, can be determined using reactive strips whose color is analyzed after the reaction.

These strips include a small area covered with a compound comprising a specific reagent for the substance whose concentration is to be evaluated and secondary reagents which are pigments colored according to the concentration of the substance to be evaluated.

The use of these reactive strips is well known and may be subdivided as follows:

A droplet freshly sampled at a fingertip or at the ear is first of all deposited on the reactive area. The reaction is then allowed to proceed for a determined time, which can vary. The blood is then removed either by washing or by wiping and there is a wait for a new period of time which is also determined. Finally, a color measurement is performed using a reflectometer. The result obtained is compared directly with a chart and is converted into a product concentration.

The use of this process requires a number of instruments.

The sampling of the drop of blood is performed with the aid of an auto-pricker. This device is intended to impart a rapid movement to a dart equipped with a sterile point which enables it to pierce superficially the skin of the finger or of the ear on which it has been placed. This pricking makes it possible to collect the drop of blood needed for the analysis. The dart is generally protected by the body of the auto-pricker when at rest. Its movement is obtained by the action of a pretensioned main spring. A secondary spring, compressed during the action of the main spring ensures the return of the small lance to its initial location inside the auto-pricker body. A number of models of auto-prickers are currently available, the body of the most recent one is shaped like a fountain pen.

The strips are generally distributed in a tube.

The control of the reaction times before and after the wiping of the blood requires the use of a stopwatch.

The measurement of the color of the reactive area is carried out with a reflectometer. It comprises a monochromatic light source and a diode receiver, and means enabling the intensity of the reflected light to be converted into the value of the parameter to be measured. It comprises a display device allowing the result to be seen.

Certain reflectometers incorporate a stopwatch which enables the number of instruments needed to perform measurements to be reduced.

SUMMARY OF THE INVENTION

The objective of the invention is the design of a device for blood sampling and analysis which allows all the abovementioned operations to be carried out in a very simple manner and which is easily portable.

Another objective of the invention is to provide an apparatus which can be manipulated with a single hand while, for example, the other is used for the puncture.

To this end, the device for blood sampling and analysis of the invention comprises an auto-pricker, a magazine for strips, these strips comprising a reactive area, and a reflectometer. The magazine is integral with the auto-pricker and the device comprises means for making the reflectometer and the auto-pricker integral when at rest.

According to a preferred embodiment of the invention, the auto-pricker and the reflectometer comprise complementary members enabling them to be made integral by nesting when the color of the reactive area is being read by the reflectometer.

BRIEF DESCRIPTION OF THE DRAWINGS

The invention will be described in detail with reference to the figures, in which:

FIG. 1 shows a sectional view of the integral device in a position of rest according to a first embodiment, FIG. 2 shows a sectional view of the integral device in a position of rest according to a second embodiment.

DESCRIPTION OF THE PREFERRED EMBODIMENT

Figure 3:
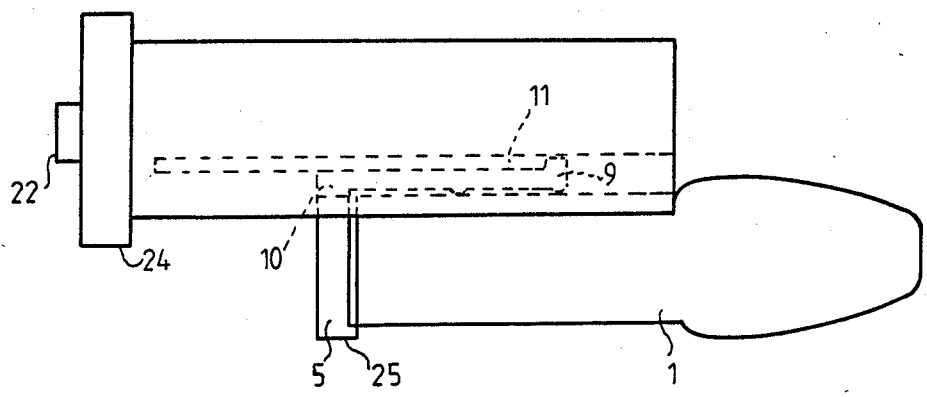
FIG. 3 shows a sectional view of the integral device in a reading position.
Figure 6:
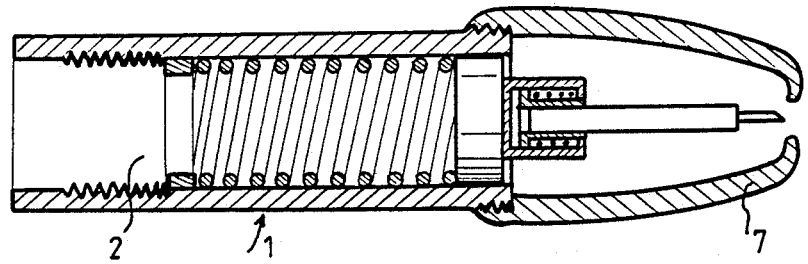
FIG. 6 shows a sectional view of the auto-pricker component.
Figure 4:
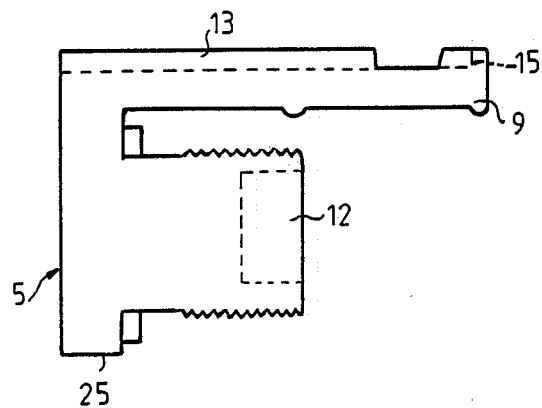
FIG. 4 shows a view of the disposable plug in vertical section.
Figure 5:
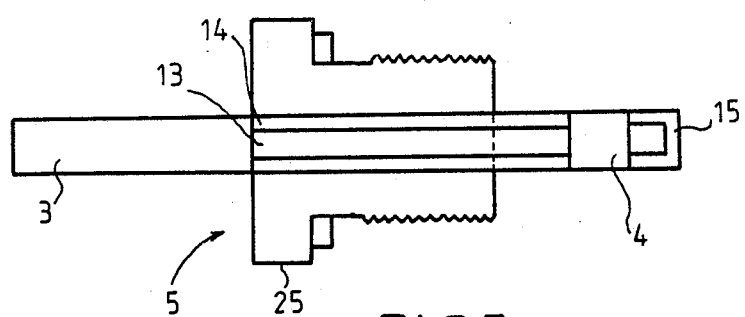
FIG. 5 shows a bottom view of the disposable plug, and of a reactive strip.
Figure 7:
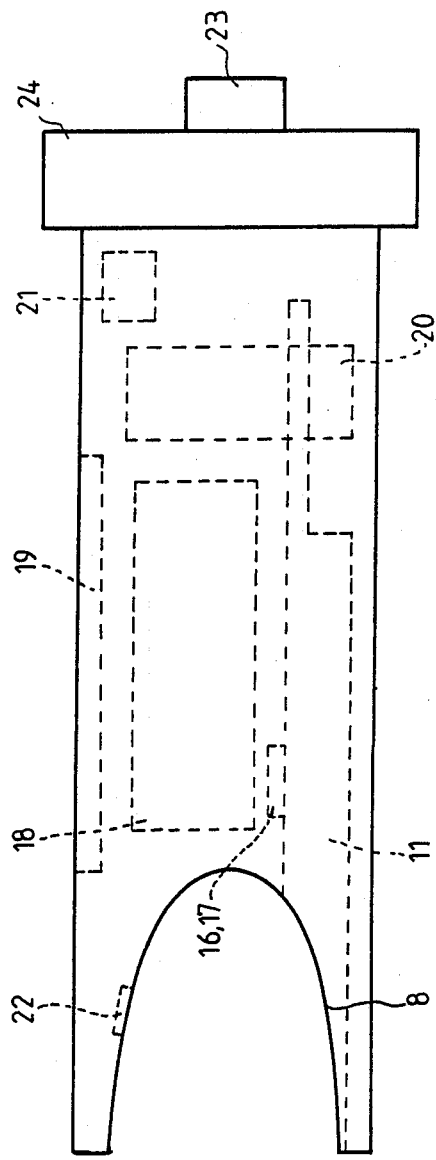
FIG. 7 shows a top view of the reflectometer.

The device for blood sampling and analysis comprises an auto-pricker 1, and a magazine 2 for strips. These strips comprise a thin support 3 generally made of flexible plastic, on which a reagent is deposited, forming a reactive area 4. The magazine 2 is integral with the auto-pricker 1. It consists of a housing provided within the body itself of the auto-pricker 1. This magazine 2 is closed by a plug 5. The reflectometer 6 and the auto-pricker 1 have complementary shapes constituting means which make it possible to make one integral with the other when at rest. These components 7 and 8 are preferably slightly conical and at least one of them being capable of slight elastic deformation enabling one to be made integral with the other by wedging. The ends 7 and 8 of the auto-pricker can also comprise other means of integrating such as complementary screw threads or a groove which can interact with a protuberance by snap fastening, etc.

Thus, when at rest, the device of the invention forms a single entity which is very simple to handle. The reflectometer 6, as well as the auto-pricker 1, may be of substantially cylindrical elongate form, so that the device of the invention can then be easily stowed away in a pocket, like a fountain pen. The plug 5 may, furthermore, be provided with a clip 9, allowing the device to be hooked inside a pocket.

In another embodiment, shown in FIG. 2, the reflectometer may be of a more compact form, substantially circular to square and may be equipped with a neck cord which enables the user to hang it around his neck.

The auto-pricker 1 and the reflectometer 6 also comprise complementary components 10 and 11 enabling them to be made integral by nesting during the reading of the color of the reactive area 4 of the strip 3 by the reflectometer 6. The device can thus be easily manipulated both when it is at rest and during the reading stage.

The reagents carried by the strip are highly moisture-sensitive. In order to improve their conservation, the magazine 2 comprises a disposable plug 5 which incorporates a desiccator 12. This plug 5 may be supplied at the same time as the refill strips, so that the desiccator 12 is always active.

The disposable plug 5 is provided with a groove 13 intended to receive and to hold the strip 3. This groove 13 comprises edges 14 on which the strip can be engaged and is thus perfectly held. The reactive area 4 is accurately positioned when the strip 3 abuts at the bottom 15 of the groove 13.

During the sampling it is also possible to place a strip 3 in the groove 13; the auto-pricker 1 is then held in one hand in order for the sampling to be done with the other hand. After pricking, a drop of blood is deposited onto the strip 3 at the location of the reactive area 4.

The groove 13 is preferably left clear in the region of the reactive area 4. This is to say that the edges 14 and the flanks of the grooves 13 are interrupted in this region. The deposition of the drop of blood on the reactive area 4 is thus made easier, as is its wiping after the necessary reaction time.

According to this arrangement, the support of the strip 3 consists of the disposable plug 5. This is particularly advantageous because, following a certain number of samplings the strip support is unavoidably soiled. In this way, it is renewed at regular intervals.

According to a preferred embodiment, the clip 9 of the disposable plug 5 carries the groove 13.

According to a particularly advantageous embodiment, the component 10 of the auto-pricker complementary with the component 11 of the reflectometer and allowing these two componenents to be made integral by nesting during the reading consists of the clip 9. The component 11 of the reflectometer then consists of a groove 11. The nesting of the clip 9 in the groove 11 thus permits an accurate positioning of the reactive area 4 of the strip 3 relative to the light source 16 and to the diode receiver 17. The measurement is therefore carried out under optimum conditions in this way.

The reflectometer 6 additionally comprises a processing system 18, a display system 19, a stopwatch 20 and a sonic device 21.

The processing device comprises a converter translating the intensity of the reflected light for a wavelength over a time, a logic calculation which enables this time to be converted into the value of the parameter to be measured in comparison with the data entered in a read-only memory and corresponding to a chart.

This read-only memory can additionally perform other functions, such as memorizing the latest results, the time at which they have been obtained and, if desired, communication with a more powerful calculator responsible for processing these results.

The nesting of the auto-pricker and of the reflectometer in a rest position is responsible for cutting the electrical circuit of the reflectometer by means of a switch 22. Conversely, their separation ensures that a voltage is applied thereto. The plug 23 is employed for starting the stopwatch and the sound alarm comes on when the elapsed time corresponds to the preprogrammed periods needed for the reaction before and after wiping. The knurled wheel 24 allows the stopwatch to be set.

According to a preferred embodiment, the disposable plug 5 comprises a plane face 25 which makes sure the device is stable both in a rest position and in a reading position, when it is placed on a planar horizontal surface.

What is claimed is:

1. A device for sampling blood and evaluating desired concentrations of substances therein, comprising:
    an auto-pricker;
    a plurality of strips, said strips including a reactive area having a color which varies according to the concentration of the substance being evaluated;
    a reflectometer comprising:
        (a) reading system means for supplying information about said reactive area;
        (b) processing system means for receiving and processing said information supplied by said reading system means, said processing system means comprising microprocessor and read-only memory means for converting said information supplied by said reading system into the desired concentration; and
        (c) display system means for directly displaying the desired concentration; and
    magazine means for holding said strips, said magazine means being integral with said auto-pricker and having holder means for receiving one of said strips externally of said reflectometer before said one of said strips has received the sampled blood;
    said auto-pricker being separable from said reflectometer during pricking, and said auto-pricker and said reflectometer including first integration means for integrating said auto-pricker and said reflectometer when at rest and second integration means for integrating said auto-pricker and said reflectometer during reading of the color of said reactive area.

2. The device of claim 1, wherein said second integration means comprises complementary means for nesting said auto-pricker in said reflectometer during reading of the color of said reactive area.

3. The device of claim 1, wherein said auto-pricker and said reflectometer include tensioning means for triggering said reflectometer only when said auto-pricker and said reflectometer are made integral during reading of the color of said reactive area.

4. The device of claim 1, wherein said magazine means includes a disposable plug incorporating desiccator means for absorbing moisture to conserve said strips.

5. The device of claim 1, wherein said magazine means comprises a disposable plug provided with first groove means for receiving one of said strips before said one of said strips has received the sampled blood, wherein said plug includes clip means for carrying said first groove means, and wherein said reflectometer includes second groove means for receiving said clip means and positioning said reactive area of said one of said strips relative to said reading system means of said reflectometer when said reflectometer is in use.

6. The device of claim 1, said reflectometer further comprising: (d) a stopwatch and (e) a sonic device.

7. The device of claim 4, wherein said plug includes planar face means for resting said device when said device is at rest and when said reflectometer is being used.

8. A device for sampling blood and evaluating desired concentrations of substances therein, comprising:
    an auto-pricker;

a plurality of strips, said strips including a reactive area having a color which varies according to the concentration of the substance being evaluated;

a reflectometer comprising:
- (a) reading system means for supplying information about said reactive area;
- (b) processing system means for receiving and processing said information supplied by said reading system means, said processing system means comprising microprocessor and read-only memory means for converting said information supply by said reading system into the desired concentration; and
- (c) display system means for directly displaying the desired concentration; and magazine means for holding said strips, said magazine means being integral with said auto-pricker and including a disposable plug provided with groove means for receiving one of said strips externally of said reflectometer before said one of said strips has received the sampled blood;

said auto-pricker and said reflectometer including integration means for integrating said auto-pricker and said reflectometer when at rest and during reading of the color of said reactive area.

9. The device of claim 8, wherein said groove means includes edge means for accurately positioning said reactive area and said edge means is interrupted at said reactive area to facilitate depositing the sampled blood on said reactive means and wiping it off.

10. The device of claim 8, wherein said plug includes clip means for carrying said groove means.

11. The device of claim 10, wherein said reflectometer includes additional groove means for receiving said clip means and positioning said reactive area of said one of said strips relative to said reading system means of aid reflectometer when said reflectometer is in use.

* * * * *